Sept. 15, 1959 M. MALANDRONE Plant Pat. 1,864
ROSE PLANT
Filed Dec. 31, 1958
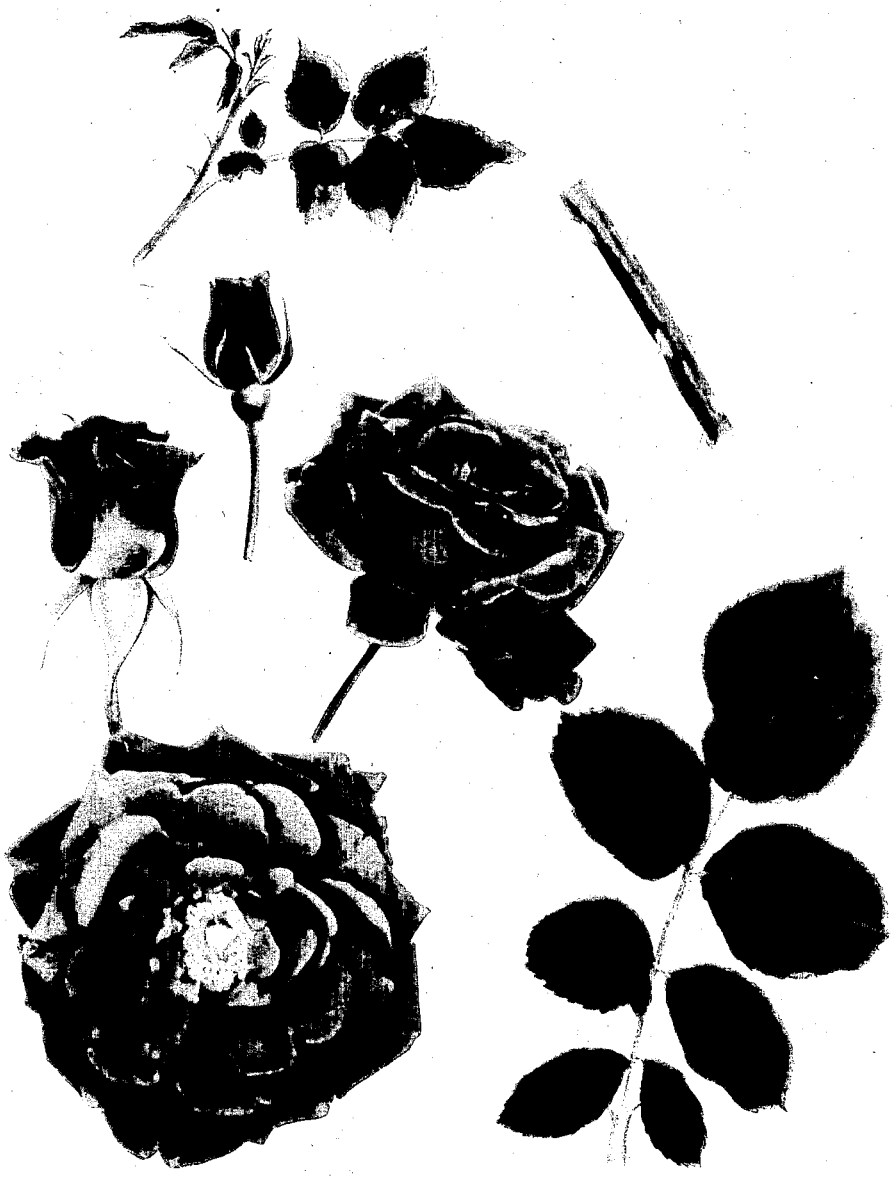
Inventor.
Michele Malandrone
By: Robb & Robb
Attorneys.

United States Patent Office

Plant Pat. 1,864
Patented Sept. 15, 1959

1,864

ROSE PLANT

Michele Malandrone, Sessant D'Asti, Italy

Application December 31, 1958, Serial No. 784,413

1 Claim. (Cl. 47—61)

The present invention relates to a new and distinct variety of rose plant of the climber class, which was originated by me by crossing an unnamed and unpatented seedling of "New Dawn" (U.S. Plant Patent No. 1) with "New Yorker" (U.S. Plant Patent No. 823).

The primary objective of this breeding was to produce a new rose variety which combines ever-blooming, hardy and climbing habits with a flower size equivalent to that of hybrid tea class roses. This objective was fully achieved, along with other desirable improvements, as evidenced by the following characteristics which are outstanding in the new variety and distinguish it from its parents, as well as from all other varieties of which I am aware:

(1) Hardy, healthy, vigorous, ever-blooming and climbing habits of growth;

(2) Large flowers averaging 5 inches in diameter;

(3) Strong tea fragrance;

(4) A general color tonality of the flowers corresponding to Carmine, lightly overcast with Oxblood Red; and (5) Long-lasting and unfading color of the flowers.

Asexual reproduction of the new variety by budding, as performed at Newark, New York, U.S.A. and also at Pleasanton, California, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.

*Seed parent.*—An unnamed seedling of "New Dawn."

*Pollen parent.*—"New Yorker."

Classification:

*Botanic.*—Climber.

*Commercial.*—Climber.

*Flower*

(Observations made from specimens grown outdoors at Newark, New York, U.S.A. in the early afternoon near the middle of August.)

Blooming habit: Recurrent—continuous.

Bud:

*Size.*—Medium.

*Form.*—Ovoid; is not affected by wet or hot weather.

*Color.*—When sepals first divide—Bordeaux, Plate 12. When petals begin to unfurl—Oxblood Red, Plate 1. When half-blown: inside of petals—Carmine, Plate 1, lightly overcast with Maroon, Plate 1; reverse of petals—Carmine, Plate 1, lightly overcast with Oxblood Red, Plate 1.

*Sepals.*—Slightly branched; curl back when petals begin to unfurl. Color: inside—Corydalis Green, Plate 41; outside—Light Elm Green, Plate 17, lightly overcast with Van Dyke Red, Plate 13.

*Calyx.*—Color—Biscay Green, Plate 31. Shape—pear. Size—small. Aspect—smooth. Odor when rubbed—none.

*Peduncle.*—Length—medium. Aspect—smooth. Strength—erect; heavy. Color—Brick Red, Plate 13.

*Opening.*—Opens up well; is not affected by adverse weather conditions.

Bloom:

*Size.*—Large. Average size when fully expanded—5 inches.

*Borne.*—Both singly and several together.

*Stems.*—Medium length; strong.

*Form (when first open).*—Cupped. Permanence—retains its form to the end.

*Petalage.*—Double (full but open center). Number of petals under normal conditions—35.

*Color.*—Center of flower—Carmine, Plate 1. Outer petals—Carmine, Plate 1, lightly overcast with Oxblood Red, Plate 1. Base of petals (aiglet)—Amber Yellow, Plate 16. Inside of petals—Carmine, Plate 1, lightly overcast with Oxblood Red, Plate 1. Reverse of petals—Pomegranate Purple, Plate 12, lightly overcast with Spinel Red, Plate 26. General tonality from a distance—Carmine, Plate 1.

*Discoloration.*—General tonality at end of first day—Carmine, Plate 1, lightly overcast with Oxblood Red, Plate 1. Second day—Carmine, Plate 1, lightly overcast with Oxblood Red, Plate 1. Third day—Carmine, Plate 1, lightly overcast with Oxblood Red, Plate 1.

Petals:

*Texture.*—Thick; is not affected by wet or hot weather.

*Appearance.*—Inside—velvety. Outside—satiny.

*Form.*—Oval.

*Arrangement.*—Imbricated (regularly arranged shingle-like).

*Petaloids in center.*—Few; large.

*Persistence.*—Drop off cleanly.

*Fragrance.*—Strong. Nature—tea (average hybrid tea scent).

*Lasting quality.*—On the plant—very long. As cut flower—long.

*Genital organs*

Stamens, anthers: Medium size; many; regularly arranged around styles. Color—Light Orange-Yellow, Plate 3.

Stamens, filaments (threads): Medium length. Color—Spinel Red, Plate 26.

Pollen: Color—Pale Yellow-Orange, Plate 3.

Styles: Bunched; uneven length; medium length; thin.

Stigmas: Color—Naples Yellow, Plate 16.

Ovaries: All enclosed in calyx.

Hips: None.

Seeds: None.

*Plant*

Form: Climber.

Growth: Very vigorous (attains a height of from 8 to 10 feet); upright.

Foliage: Compound of 5 to 7 leaflets.

*Size.*—Large.

*Quantity.*—Normal.

*Color.*—New foliage: upper side—Garnet Brown, Plate 1; under side—Nopal Red, Plate 1. Old foliage: upper side—Elm Green, Plate 17; under side—Light Hellebore Green, Plate 17.

*Shape.*—Oval pointed.

*Texture.*—Upper side—leathery. Under side—smooth.

*Ribs and veins.*—Ordinary.

*Edge.*—Serrated.

*Serration.*—Both double and single; small.

*Leaf stem.*—Color—Eugenia Red, Plate 13. Under side—prickly.

*Stipules.*—Medium length; slightly bearded.

Wood:

*New wood.*— Color—Turtle Green, Plate 32, lightly overcast with Eugenia Red, Plate 13. Bark—smooth.

*Old wood.*—Color—Light Bice Green, Plate 17. Bark—smooth.

Thorns:

*Thorns.*—Quantity: on main stalks from base—ordinary; on laterals from stalk—ordinary. Form— flat base; medium length; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the climber class, substantially as herein shown and described, characterized particularly as to novelty by the unique combination of hardy, healthy, vigorous and ever-blooming habits of growth, large flowers, strong Tea fragrance of the flowers, a general color tonality of the flowers corresponding to Carmine, lightly overcast with Oxblood Red, and the long-lasting and unfading qualities of the flower color.

No references cited.